United States Patent [19]

Hannart

[11] 4,173,635

[45] Nov. 6, 1979

[54] HYPOTENSIVE AJMALICINE DERIVATIVES

[76] Inventor: Jean A. A. J. Hannart, 98, Avenue De Fré, Brussels, Belgium

[21] Appl. No.: 880,731

[22] Filed: Feb. 24, 1978

[30] Foreign Application Priority Data

Feb. 28, 1977 [FR] France .................................. 77 5826

[51] Int. Cl.² .................. A61K 31/445; C07D 491/22
[52] U.S. Cl. ...................................... 424/256; 546/41
[58] Field of Search ...................... 260/293.55, 293.53; 428/256, 262; 548/359

[56] References Cited

U.S. PATENT DOCUMENTS 2,046,432  7/1936  Senn ..................................... 548/359

OTHER PUBLICATIONS

March, J., *Advanced Organic Chemistry*, McGraw-Hill, New York, 1968, pp. 589-590.

Primary Examiner—Natalie Trousof
Assistant Examiner—Richard A. Schwartz
Attorney, Agent, or Firm—Pollock, Vande Sande & Priddy

[57] ABSTRACT

The invention relates to new derivatives of ajmalicine of the formula:

(I)

in which R represents either a hydrogen atom or a linear or branched alkyl radical having 1 to 6 carbon atoms and which may be substituted with at least one hydroxy group.

These derivatives may be prepared by reacting hydrazine or a hydrazine hydrate with ajmalicine.

These compounds may be used as hypotensive drugs.

6 Claims, No Drawings

HYPOTENSIVE AJMALICINE DERIVATIVES

The present invention relates to compounds of the general formula I given hereafter and also to the addition salts formed by these compounds with pharmaceutically acceptable inorganic and organic acids.

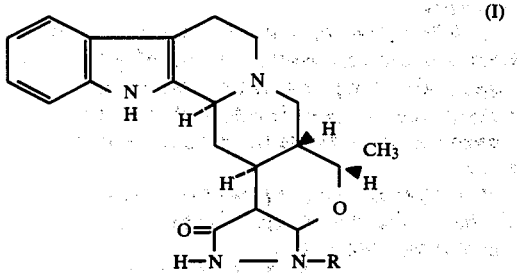

(I)

In said formula: R represents either a hydrogen atom or a linear or branched alkyl radical having 1 to 6 carbon atoms and which may be substituted with at least one hydroxy group.

The derivatives of formula I have valuable adrenaline-antagonizing properties. The invention also has for is object the therapeutic use of said derivatives.

The derivatives of formula I may be prepared by reacting hydrazine hydrate or a N-alkylated hydrazine with ajmalicine or a salt thereof. The reaction advantageously takes place by dissolving both reactants into an alkanol such as ethanol or isopropanol and heating under reflux conditions for about 24 hours.

EXAMPLE

Pyrazolo [16,17-d]oxayohimban-19α-methyl-23 one (OC-120; formula I: R=H)

A suspension is prepared containing 10 g of ajmalicine in a mixture of 10 ml of 99–100% hydrazine hydrate and 10 ml absolute ethanol. The mixture thus obtained is heated under a blanket of argon and under reflux conditions. After 24 hours, the reaction is completed. The solution obtained is evaporated to dryness and the residue of evaporation is taken up with a minimum amount of methanol and diluted with water. There is obtained a precipitate which is filtered- of, dried under vacuum and recrystallized from acetone.

Base

M.P.: 208°–210° C.
$(\alpha)_D$: $-28.5°$ (c=1, MeOH)
I.R. spectrum (KBr): bands at 3300–3400, 1590 cm$^{-1}$
U.V. spectrum λ max. (ε): 224 (36,000), 273 (7,300) 281 (7,400), 289 (6,200)
Mass spectrum: main ions at m/e 352, 351, 307, 246, 221, 184, 170, 169, 156
NMR spectrum: indole NH at 11.66 ppm doublet at 1.48 ppm 19 α-methyl.

Hydrochloride

M.P.: 264°–267° C.
$(\alpha)_D$: $-6°$ (c=0.5, MeOH)
Analysis, calculated for $C_{20}H_{26}N_4O_2Cl$

|  | % C | % H | % N |
|---|---|---|---|
| calculated | 56.46 | 6.16 | 13.17 |
| found | 55.98 | 6.19 | 13.22 |

Pharmacological and toxicological test results have shown very interesting properties of the derivatives according to the present invention.

OC-120 at a dose of 50 γ completely antagonizes the contracture-producing effect of adrenaline on the vas deferens of guinea pig.

At the same dose (50 γ), phentolamine or 2-[N-(m-hydroxyphenyl)-p-toluidinomethyl] imidazoline shows a two times smaller activity.

At 10 γ, OC-120 reduces to half its value the contracture-producing effect of adrenaline on the uterus of a female rat treated with the compound. Under the same conditions, phentolamine has the same effect at a dose of 20 γ. On the nictitating membrane of cat, OC-120 when administered intravenously at a dose of 250 γ/kg antagonizes for more than one hour the contractions due to adrenaline.

Phentolamine at a dose of 1 mg/kg antagonizes these contractions for 15–20 minutes. By rabbits, OC-120 at a dose of 300 μg/kg i.v. completely antagonizes the hypertensive effect obtained by means of a continuous perfusion of hypertensine at 2 μg/kg. At the same dose, this effect is only partly antagonized by phentolamine.

OC-120 thus has anti-adrenergic properties which are stronger than those of phentolamine. Its therapeutic use as hypotensive agent and also against cardiovascular effects of stress may be contemplated.

The above tests thus show that the derivatives of the invention may be used as hypotensive drug.

For that purpose they may be administered by general, oral or parenteral route. The dosage of the drug is from 10 to 30 mg of active ingredient to take in 24 hours.

Hereafter non limiting examples of drug composition are given.

Tablets

Active ingredient 0.010 g

| carrier: | talc | |
|---|---|---|
| | fatty acid ester | to make a tablet |
| | potato starch | |
| | scarlet G.N. | |

Injectable phials

Active ingredient (hydrochloride) 0.015 g
"Pro injectione" solution: sufficient amount.

What I claim is:

1. Derivative of ajmalicine of the formula:

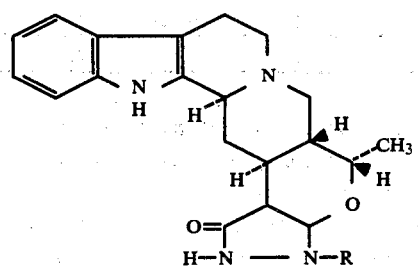

wherein R represents either a hydrogen atom or a linear or branched alkyl radical having 1 to 6 carbon atoms and which may be substituted with one hydroxy group.

2. An addition salt formed by said derivative of claim 1 with a pharmaceutically acceptable inorganic or organic acid.

3. A derivative according to claim 1, which consists of pyrazolo [16, 17-d] oxayohimban -19α-methyl-23 one (formula I: R=H).

4. A hypotensive composition comprising as the active ingredient, a compound as defined in claim 1 or a pharmaceutically acceptable acid salt thereof or mixtures thereof in an effective hypotensive amount together with a pharmaceutically acceptable carrier or excipient.

5. A hypotensive composition according to claim 4 having a adrenaline-antagonizing effect, for use as a hypotensive drug and against the cardio-vascular effects of stress to provide a dose of 10 to 30 mg of active ingredient in 24 hours by general, oral or parenteral route.

6. A hypotensive composition according to claim 4 in the form of tablets or injectable phials containing 10–15 mg of active ingredient.

* * * * *